US009476832B2

(12) United States Patent
Walla et al.

(10) Patent No.: US 9,476,832 B2
(45) Date of Patent: Oct. 25, 2016

(54) HIGH RESOLUTION LIGHT MICROSCOPE

(71) Applicant: Technische Universitaet Braunschweig, Braunschweig (DE)

(72) Inventors: Peter J. Walla, Braunschweig (DE); Nour Hafi, Braunschweig (DE)

(73) Assignee: TECHNISCHE UNIVERSITAET BRAUNSCHWEIG, Braunschweig (DE)

( * ) Notice: Subject to any disclaimer, the term of this patent is extended or adjusted under 35 U.S.C. 154(b) by 118 days.

(21) Appl. No.: 14/362,346

(22) PCT Filed: Dec. 5, 2012

(86) PCT No.: PCT/EP2012/074576
§ 371 (c)(1),
(2) Date: Sep. 4, 2014

(87) PCT Pub. No.: WO2013/083665
PCT Pub. Date: Jun. 13, 2013

(65) Prior Publication Data
US 2014/0367590 A1 Dec. 18, 2014

(30) Foreign Application Priority Data

Dec. 5, 2011 (DE) .................. 10 2011 087 770

(51) Int. Cl.
| G02B 21/16 | (2006.01) |
| G01N 21/64 | (2006.01) |
| G02B 21/00 | (2006.01) |
| G02F 1/01 | (2006.01) |
(Continued)

(52) U.S. Cl.
CPC ...... *G01N 21/6445* (2013.01); *G01N 21/6458* (2013.01); *G02B 21/0068* (2013.01);
(Continued)

(58) Field of Classification Search
CPC .............. G01N 21/6445; G02F 1/136; G02B 21/0068; G02B 21/241; G02B 21/16; G02B 27/283
See application file for complete search history.

(56) References Cited

U.S. PATENT DOCUMENTS

| 2001/0045523 A1 | 11/2001 | Baer |
| 2009/0242798 A1 | 10/2009 | Bewersdorf et al. |
| 2012/0069332 A1 | 3/2012 | Frankel |

FOREIGN PATENT DOCUMENTS

| DE | 10 2006 046 111 A1 | 4/2008 |
| WO | 2011-090710 A2 | 7/2011 |

OTHER PUBLICATIONS

Ha, T., et al., "Probing the interaction between two single molecules: Fluorescence resonance energy transfer between a single donor and a single acceptor", Proceeding of the National Academy of Sciences, USA, vol. 93. Jun. 1996, pp. 6264-6268.
(Continued)

*Primary Examiner* — David Porta
*Assistant Examiner* — Faye Boosalis
(74) *Attorney, Agent, or Firm* — Greer, Burns & Crain, Ltd.

(57) ABSTRACT

The present invention relates to an apparatus for the optical analysis of a sample, also referred to as microscope, which is configured for an optical analysis process having high resolution for the detection of fluorescent molecules. The apparatus and the process applied when using the apparatus are configured for excitation light generated by an excitation light source to be directed onto a sample and the light emitted by the probe is detected. The apparatus and the process are characterized in that the excitation light is synchronized with the detection. The apparatus is characterized in that it has a polarization device which is configured to modulate the polarization of the excitation light with a modulation signal, wherein the modulation signal has or consists of at least one frequency, in particular a pre-determined frequency or several pre-determined superimposed frequencies, or the modulation signal consists of a sequence of signals that has no repetition.

22 Claims, 2 Drawing Sheets

Figure 1:
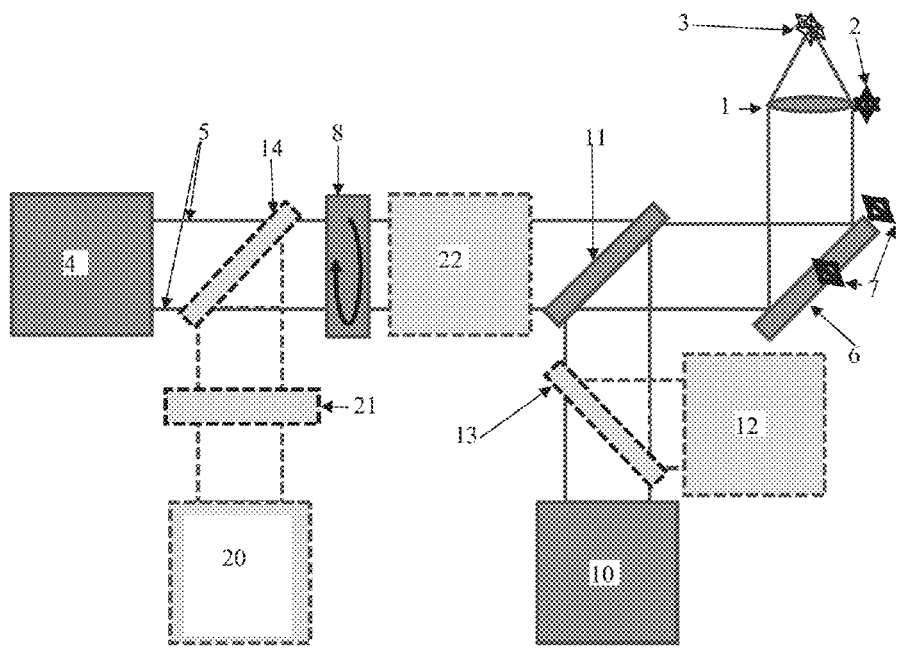

(51) Int. Cl.
  *G02B 26/06* (2006.01)
  *G02B 27/14* (2006.01)
  *G02B 27/28* (2006.01)

(52) U.S. Cl.
  CPC ........... *G02B21/0076* (2013.01); *G02B 21/16* (2013.01); *G02F 1/0136* (2013.01); *G01N 2021/6439* (2013.01); *G01N 2021/6463* (2013.01); *G02B 26/06* (2013.01); *G02B 27/141* (2013.01); *G02B 27/283* (2013.01)

(56) References Cited

OTHER PUBLICATIONS

Ha, T., et al., "Single Molecule Dynamics Studied by Polarization Modulation", Physical Review Letters, vol. 77, No. 19, Nov. 4, 1996, pp. 3979-3982.

Lacoste, Th., et al., "Contrast enhancement using polarization-modulation scanning near-field optical microscopy (PM-SNOM)", Ultramicroscopy, vol. 71, (1998), pp. 333-340.

HIGH RESOLUTION LIGHT MICROSCOPE

The present invention refers to an apparatus for the optical analysis of a sample, also referred to as microscope, which is configured for a high resolution optical analysis process for the detection of fluorescent molecules. The apparatus and the process applied by using the apparatus are arranged such that the excitation light generated by the excitation light source is focused on a sample and that the light emitted by the sample is detected. The apparatus and the process are characterized by the fact that the excitation light is synchronized with the detection. The excitation light source may consist of a laser device.

STATE OF THE ART

US 2001/045523 describes the stimulated emission depletion microscopy (STED) which involves a sample being irradiated and sampled via a microscope objective by two parallel light paths, while light emitted by the sample exits through the same optical path and is detected. One of the light beams is coupled into the optical path by means of a dichroic mirror and has an excitation wavelength which is specific to the sample's fluorescent molecules, while the second light beam, which is also coupled into the common optical path by means of a dichroic mirror, has a wavelength that is specific to the de-excitation of the sample's fluorescent molecules from their excitation state, wherein the second light beam irradiates only a ring-shaped part of the focal area. Subsequently, fluorescent molecules which are in the focus of both light beams will be de-excited by the second light beam despite the excitation by the first light beam while the excited fluorescent molecules located in the ring-shaped second light beam can emit so that only their emission is collected by the detector. For a particularly high resolution, the second light beam is irradiated in the shape of an interference pattern e.g. by means of a phase plate positioned therein, the interference pattern having a directional null in the measurement range but has otherwise reached saturation of the excited fluorescent molecules with excitation light.

This process is disadvantageous in that the device requires an extremely high precision of optical path alignment for the excitation wavelength and for the de-excitation wavelength and a time-consuming deflection of excitation light over the sample, e.g. by means of a scanner.

US 2009/0242798 A1 describes the photo-activated localization microscopy wherein fluorescent molecules are individually detected in a sample by first irradiating fluorescent molecules using a switching wavelength light so that the fluorescent molecules are excited for emission when being irradiated with an excitation wavelength light. Repeated irradiation using switching wavelength light each causes a statistically distributed selection of fluorescent molecules being excited for emission by the following irradiation with excitation wavelength light. For evaluation purposes, the subsequently detected emission maxima are determined with high spatial resolution and are superimposed.

This process is disadvantageous in that it is limited to those fluorescent molecules which are to be brought to an excitable state using a switching wavelength radiation, with time duration suitable for the analysis, and that the sequential irradiation and locating of the individual molecules is time consuming.

OBJECT OF THE INVENTION

The object of the present invention is to provide an alternative apparatus and an alternative process for the optical detection of fluorescent molecules in a sample with high resolution, preferably in the provision of an apparatus which allows a reduced configuration effort, in particular for focusing, and which allows for a process that can be performed with any molecule that is fluorescent when irradiated with an excitation wavelength, and which preferably spatially resolves a multitude of molecules. Furthermore, the process shall not be limited e.g. to fluorescent molecules that are switchable by a switching wavelength.

GENERAL DESCRIPTION OF THE INVENTION

The invention achieves this object by the features of the claims, in particular with an apparatus for optical analysis of a sample containing at least one fluorescent molecule, using an excitation light source which optionally consists of a laser that is set up to generate light of an excitation wavelength, wherein the apparatus has a beam path which is directed onto the sample by an optical element, also referred to as an objective. The apparatus is equipped with a detector adapted for detecting the radiation emitted by the fluorescent molecule, and is positioned in abeam path in which the light emitted from the sample is guided. The optical path in which the emitted light from the sample is guided is preferably directed through the same objective through which the beam path of the excitation light generated by the excitation light source is guided. In a section for excitation light adjacent to the objective, the beam path preferably runs collinear to the beam path of emitted light, e.g. in a section in which the beam path runs between the objective and a mirror, in particular a partially-transparent mirror, which orients the beam path for excitation light from the excitation light source to the objective, and/or a mirror which orients the optical path for emitted light emanating from the objective to the detector or to a mirror oriented to the detector.

The apparatus is characterized by a polarization device which is configured to modulate the polarization of the excitation light, or another feature of the excitation light, with a modulation signal, wherein the modulation signal has or consists of at least one frequency, in particular one predetermined frequency or several predetermined superimposed frequencies, or the modulation signal consists of a sequence of signals which has no repetition or no periodic repetition. Preferably the polarization is a linear polarization and the modulation is a rotation. The polarization device, which is configured according to the invention to modulate the polarization of the excitation light generated by the excitation light source, in particular with the modulation signal, to modulate e.g. into a frequency, may be referred to as a modulating device for the polarization or as a polarization modulator, wherein the polarization is modulated with the modulation signal, in particular into at least one frequency, and in embodiments may be referred to as a polarization rotation device, which in particular is controlled by the modulation signal, for example is frequency-controlled. Such a polarization modulator which is controlled by the modulation signal, preferably frequency-controlled, can be a $\lambda/2$ plate, $\lambda/4$ plate linearly movable in an angle, especially at 90° to its polarization direction, or it can as polarizing element have or consist of a circular polarization filter linearly movable at an angle, in particular perpendicular to its polarization direction. A preferred polarization modulator is polarizing element that is rotatably driven and controlled with the modulation signal, which is arranged in the beam path between the excitation light source and the objective. The rotatable polarizing element may be a linear polarization filter, especially in case of an excitation light source which is configured to generate non-polarized or circularly polarized excitation light, or a phase shift plate, preferably a λ/2 or a λ/4 plate, in case of an excitation light source which is configured to generate a linearly polarized excitation light, or a combination of inversely rotated mirrors, e.g. inversely rotated against one another by 45°, so that its rotation is controlled by the modulation signal and determines the polarization modulation of the excitation light. Alternatively, the polarization modulator can be an acoustic-optical modulator or an electro-optical modulator, in particular a Pockels cell, which is static or rotatable, controlled via the modulation signal, in particular with at least one frequency.

For the purpose of the invention, a modulation signal is a sequence of signals, in particular with a fixed respectively predetermined frequency or with at least two superimposed fixed respectively predetermined frequencies, or a series of signals which optionally have no repetition or no periodic repetition during the duration of the analytical process, or which preferably occur periodically. In general, a signal can be a sinusoidal signal, a rectangular signal and/or a sawtooth signal.

A modulation signal that consists of a sequence of signals, which has no repetition or no periodic repetition, can e.g. be a signal controlling a modulation of the polarization which passes each polarization direction at least once or exactly once, wherein the polarization is preferably modulated from an initial orientation to an identical orientation at the end of the modulation, wherein e.g. the modulation rotates a linear polarization exactly once by 180° or by 360°.

Furthermore the invention refers to a process for the optical analysis of a sample which has the steps that can be executed with the apparatus, respectively the steps for which the apparatus is configured, in particular a process for optical analysis of a sample by means of the apparatus.

By means of the modulation of the polarization of the excitation light by at least one modulation signal, which can be a time constant or a time varying frequency, the apparatus generates the excitation of a portion of the fluorescent molecules of the sample depending on the modulation signal. Because a fluorescent molecule of the sample is mainly excited for emission by the excitation light only if the polarization vector of the excitation light is oriented in parallel to the transition dipole moment vector of the fluorescent molecule. Due to the different orientation of the transition dipole moment vectors of the sample's individual fluorescent molecules, the irradiation of excitation light with a frequency-modulated polarization causes the excitation of the suitably oriented fluorescent molecules in dependence on the modulation signal. Therefore, by means of the apparatus according to the present invention in the detection process the sample's fluorescent molecules are excited according to the different orientation of their transition dipole moment vectors in dependence on the modulation signal of the polarization of the excitation light, or depending on the modulation signal used to excite the polarization modulator, respectively, and emit in a distance of time, respectively with phase shift, in dependence on the modulation signal or depending on the rotation of the polarization of the excitation light controlled by the modulation signal.

For the synchronization of the detection with the modulation of the polarization of the excitation light, the detector of the apparatus is preferably controlled in dependence on the modulation signal that controls the polarization unit, respectively in dependence on the frequency of the polarization unit, and in particular is configured for detection or isolation of the emitted light with or without phase shift, optionally with or without amplitude displacement, in at least one frequency that is equal to the modulation signal. The detection of the emission of fluorescent molecules in at least the one frequency corresponding to the modulation signal controlling the polarization modulator results in the isolation of the emission excited at the modulation signal. A preferred device for the control and/or analysis of the modulation signal controlling the polarization device, in particular the frequency of the polarization device and/or of a detector controlled in dependence on the modulation signal, is a so-called demodulator, e.g. a lock-in amplifier, or another device configured for the analysis and determination of the Fourier transformation, in particular for the simultaneous analysis and determination of the Fourier transformation of two or more detected frequencies and phases, preferably at the frequency of the modulation signal. If the polarization modulator is configured for modulation by a modulation signal consisting of a sequence of signals having no repetition or no periodic repetition, the detector is coupled with a signal analysis device that is especially configured to unfold the detected signals. This unfolding of detected signals corresponds to the demodulation at a modulation signal consisting of a sequence of signals has no repetition or no periodic repetition. Correspondingly the polarization modulator can be configured for modulation by a modulation signal which comprises or consists of exactly one period of a modulation signal, while the signal analysis device is configured for unfolding this modulation signal. In case of non-linear modulation, a signal which e.g. is modulated with exactly one or several periods of a cosine-shaped signal can also be unfolded respectively demodulated using another function as the modulation signal, e.g. a cost function.

For the purpose of the invention, such a modulation signal consisting of a sequence of signals that has no repetition or no periodic repetition is optionally comprised by the term of a frequency because such a modulation signal can e.g. be represented as a half period or as exactly one period of a frequency.

The detector is preferably coupled with a signal analysis device that is configured to exclusively collect or isolate the detected signals which are detected at least at a frequency that is identical to the modulation signal respectively to the frequency of the modulation signal.

In embodiments in which the modulation signal consists of a frequency, the signal analysis device is configured to exclusively collect and isolate the detected signals which are detected at the frequency of the polarization device.

In addition to the first detector described above, the apparatus optionally has at least one second detector onto which the light emitted by the probe is directed e.g. by means of a partially transparent mirror, and which is preferably coupled with a signal analysis device that is set up to exclusively collect or isolate those detected signals that are detected with a constant phase shift to the modulation signal which is used to control the polarization modulator, or to the modulation signal used by the polarization modulator to modulate polarization of the excitation light. A partially transparent mirror generally is e.g. a polarization beam splitter. In the process, such a detector collects different components of the light emitted by the fluorescent molecules, preferably the polarization which is random according to the different orientation of the transition dipole moment vectors of the fluorescent molecules and Which therefore results in a scattered detection of fluorescent molecules. In embodiments having a first and at least one second detector that are each coupled to a signal analysis device, from the different phase shift, modulation amplitude and the medium intensity of the light emitted by the fluorescent molecules which the two signal analysis devices collect and isolate, a higher spatial resolution of individual molecules is achieved.

Preferably the detector and/or the second detector are an area detector, e.g. a CCD camera, which offers the benefit of simultaneously collecting a large number of molecules. Optionally the detectors can be area sections of an area detector. Also in embodiments in which the detectors are area detectors or sections of an area detector, the apparatus can have a device for deflecting the excitation light across the sample, such as e.g. a scanner. The device for deflecting the excitation light can be located at any position in the beam path of the apparatus, in particular between an objective, which directs the light onto the sample, and a controlled polarization device.

The excitation light source preferably consists of a laser. The polarization modulator has a polarization device controlled by a modulation signal, or it consists of a polarization device controlled by the modulation signal, in particular a frequency-controlled polarization device. Preferably, a polarization device is used which linearly polarizes the excitation light. The polarization device controlled by the modulation signal is positioned in the beam path between the excitation light source and the objective, and it can be a linear polarizer rotating with the modulation signal, in particular a linear polarizer rotating with a frequency.

Optionally the excitation light source can be pulsed; in particular it can consist of 1 pulsed laser.

With general preference, the modulation signal into which the polarization modulator modulates the polarization, and/or which is used to control the polarization modulator, is predetermined.

Optionally the light source can be configured to generate excitation light of one or of at least two light frequencies the sum of which is equal to the frequency of the excitation light that is specific for the fluorescent molecule, in particular when using the apparatus as a microscope for the so-called two photon excitation or multiple photon excitation. In embodiments in which the light source is configured to generate the excitation light with light frequencies the sum of which is equal to the frequency of the excitation light that is specific for the fluorescent molecules, multiple photon excitation is implemented, which has the benefit of a smaller angle range in which the fluorescent molecules are suitably oriented so that a higher resolution results.

Optionally the apparatus, in addition to the aforementioned first excitation light source can have one second, or more light sources which can be additional excitation light sources. The beam path of the additional light sources is preferably directed via a dichroic beam splitter into the same objective into which the beam path of the first excitation light source is directed. In the optical path of the additional light source, a polarization modulator controlled by the modulation signal, especially a frequency-controlled polarization modulator, is arranged Which may be formed identically to the first polarization modulator located in the beam path of the first excitation light source, and which may preferably be set up to modulate the polarization with or without phase shift, optionally using the same modulation signal or in the same frequency as the polarization of the excitation light of the first light source.

Alternatively the second light source can be configured to generate light of a de-excitation wavelength. This light of a de-excitation wavelength generally effects the transition of the status of the fluorescent molecules produced by the excitation light to a status of lower energy from which no emission is possible and which therefore can be called a light for quenching of the emission produced by the excitation light and it can e.g. have a wavelength which de-excites only a certain type of molecule, or several or even all types of molecules.

Special preference is on an apparatus where the first and the second light source are linearly polarized, with the polarization of the de-excitation light beam having an angle of >0 to <180°, preferably 60° to 120°, in particular 90° to the polarization of the excitation light beam, e.g. by means of a polarization modulator located in their beam path. In this embodiment, only those fluorescent molecules are not de-excited whose transition dipole moment vectors exactly match the polarization of the excitation light beam so that the angle range of the suitably oriented fluorescent molecules is drastically reduced so that as a consequence individual molecules have a much better resolution and can be better distinguished.

In this embodiment, the polarization modulator is preferably positioned in the common beam path of the linearly polarized excitation light, source and de-excitation light source, and is configured to simultaneously modulate with the modulation signal the polarization direction of the excitation light and of the de-excitation light at constant angles between the two polarization devices.

The polarization of the excitation light is preferably oriented in an angle of 90° to the polarization of the de-excitation light so that the polarization directions of the light from the excitation light source and from the de-excitation light source are at 90° to each other. In this embodiment the polarization modulator can have a polarization rotation element consisting e.g. of a $\lambda/2$-plate, which is suitable for the wavelengths of both light sources. In a preferred embodiment the apparatus has a first light source and a second light source which are configured to produce parallel linearly polarized light which is deflected into a common beam path by means of a dichroic mirror that is directed onto a polarization modulator, e.g. a frequency-controlled, rotating $\lambda/2$ plate wherein subsequently the optical beam is directed onto an optical device which is configured to split off a wavelength range as partial beam, to rotate its polarization e.g. by 30-150°; more preferable by 60-120°, in particular by 90°, and to direct this partial beam in parallel with the non-split off partial beam onto the optical element that focuses the optical path on the sample. Accordingly, the polarization device of the de-excitation light is preferably controlled by the same modulation signal as the polarization device of the excitation light.

Additionally or optionally, de-excitation light can be directed into the objective which in particular is a microscopic objective, that illuminates only parts of the focal area. Optionally and in addition to the modulation of the polarization, de-excitation light in the form of an interference pattern is directed on the sample which has a directional null at the measurement position, and outside this position has an intensity which achieves a saturation of the fluorescent dye at the de-excitation of the excited status generated by the excitation light. For a particularly high resolution this can be achieved by an additional second light beam of a de-excitation wavelength e.g. by means of a phase plate arranged therein which produces an interference pattern with a directional null and which in the other focal area has sufficient intensity for the saturation of the excited fluorescent molecules with de-excitation light. The directional null of the de-excitation light at this point allows for the emission by the fluorescent molecules. The phase plate is preferably configured to radiate ring-shaped de-excitation light on the sample around a central directional null area which particularly is in the focus.

Alternatively or additionally the apparatus in the beam path of the excitation light source can have a first dividing mirror which deflects a part of the excitation light, in particular by 45°, and a second dividing mirror to which the partial beam separated from the first partially transparent dividing mirror is directed into the optical path to which the non-deflected partial beam is directed, wherein another polarization modulator, a phase shift element, and/or a polarization rotation element is arranged in the optical path of the deflected partial beam.

After the first dividing mirror, the beam path of the deflected partial beam is directed to the second dividing mirror, e.g. by means of a first and a second deflection mirror, wherein e.g. another polarization modulator, a phase shift element, and/or a polarization rotation element may be arranged between the deflection mirrors or between one deflection mirror and one of the dividing mirrors.

In a further embodiment the apparatus has a deflection device in the beam path in front of the objective which is controlled with special preference to direct the beam path into the objective according to a predefined pattern, in particular to guide the beam path over the sample in a predefined pattern in order to consecutively scan segments of the sample with the bean. Such an optional deflection element, which in particular is a controllably deflectable mirror, which directs the beam path pointed at the objective to the objective and which preferably also guides the light emitted by the fluorescent molecules into a beam path with identical orientation, the apparatus preferably has an analysis unit that is configured to arrange the detection signals collected during the controlled guidance of the beam path across the sample according to the controlled guidance. This way the apparatus is set up for scanning a sample. This embodiment is preferred for embodiments in which the detectors are no area detectors or segments of an area detector.

Optionally the apparatus can have an analysis unit that is configured to display in a common presentation the emission maxima of the emission signals detected at least at one frequency which depends on the modulation signal.

In general the process is described by the configuration of the apparatus. The process for optical analysis of a sample containing at least one fluorescent molecule comprises the irradiation of light on the sample, the light having an excitation wavelength that is specific for the fluorescent molecule for excitation of emission and the detection of the radiation emitted by the fluorescent molecule, wherein preferably the beam path, in which the emitted radiation is guided, is directed through the same objective through which the beam path of the excitation wavelength light is guided, as described with reference to the apparatus. The polarization or another property of the excitation light is modulated with a modulation signal which can have or consist of one frequency, several superimposed frequencies. As described with reference to the apparatus, the modulation signal can also consist of a sequence of signals that has no repetition, e g. of one portion of 180° to 360° of a period of a trigonometric function. The polarization of the excitation light can be modulated by means of a polarization device that is controlled by a modulation signal.

Optionally light of a de-excitation wavelength and/or light of a switching wavelength can be irradiated on the sample. With preference, the light of a de-excitation wavelength is polarized in an angle of >0° to <180°, in particular from 30° to 120°, preferably 90° with reference to the polarization of the excitation wavelength. With preference, the polarization of the light of the de-excitation wavelength and/or the light of the switching wavelength is modulated with the same modulation signal as the light of the excitation wavelength.

The detection of emission is synchronized with the modulation of the polarization of the excitation light, e.g. the detection of emission is controlled by the modulation signal so that the emission can be isolated which is detected with or without phase shift to the modulation signal. This control of the detection of emission by the modulation signal can be called demodulation, or, in case of a modulation signal that has no repetition, as unfolding. A modulation signal that has no repetition may e.g. comprise or consist of exactly one period of a trigonometric function, while the signal analysis is done by unfolding this modulation signal.

Furthermore the invention refers to a microscopic representation which is obtainable by the process according to the invention and which is generated in particular by using the apparatus. The microscopic representations obtainable by the process according to the invention are characterized by showing a substantially higher resolution, especially at the same magnification and numeric aperture of the objective.

DETAILED DESCRIPTION OF THE INVENTION

Figure 2:
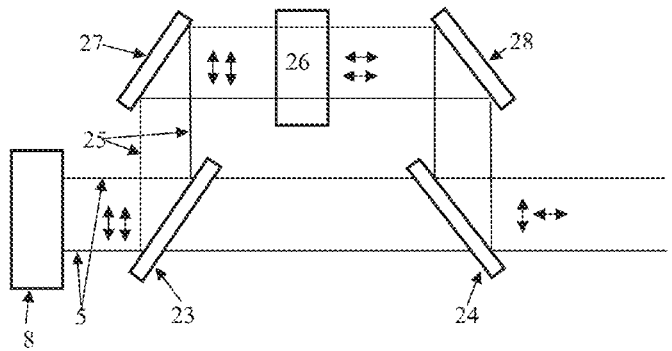
Figure 3:
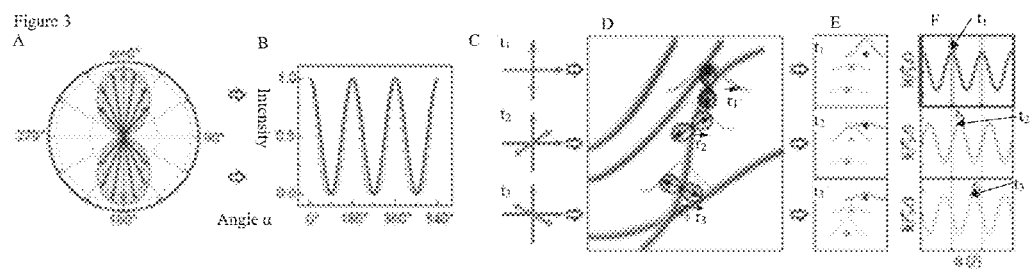
Figure 4:
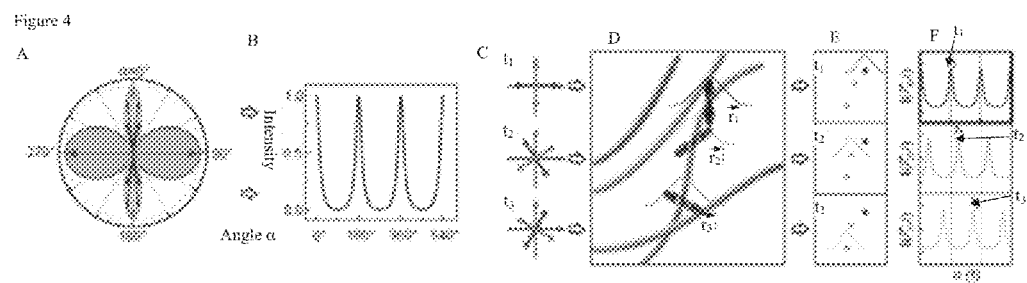

The invention is now described in more details with reference to the figures that schematically show in FIG. 1 an embodiment, FIG. 2 a section of a preferred embodiment, FIG. 3, A to F, the modulation and demodulation in an embodiment of the process with excitation light only, and FIG. 4, A to F, the modulation and demodulation in an embodiment of the process with excitation light and de-excitation light.

Using the focusing device 2, objective 1 can be focused on sample 3 which contains fluorescent molecules. An excitation light source 4 produces excitation light 5 the beam path of which is directed into the objective 1, shown here by means of a mirror 6 that is deflecting and controlled by means of the control device 7, e.g. for controlled guidance of excitation light 5 over sample 3.

The polarization modulator 8 is configured to modulate the polarization of the excitation light 5, which preferably is a linear polarization direction, with at least one frequency which represents the modulation signal. As indicated by the arrow, the polarization modulator 8 can be a $\lambda/2$ plate rotating perpendicularly to the beam path of excitation light 5.

A first detector 10 is arranged in the beam path formed by objective 1, emitted by sample 3, by a first dichroic mirror 11 deflecting from the confocal section of the beam path emitted light exiting from objective 1. An optional second detector 12 can be directed to the emitted light by one part of the emitted light being deflected from a second partially transparent mirror 13 to the second detector 12. The second partially transparent mirror preferably is a polarization beam splitter 13. As shown in the figure, the second partially transparent mirror or polarization beam splitter 13 can be arranged in the section of the optical path that is situated between the first dichroic mirror 11 and the first detector 10, or in another section of the optical path.

First detector 10 and second detector 12 are each coupled with an analysis unit which preferably filters only signals which are modulated with a frequency equal to the modulation signal that is used to control the polarization modulator 8. The analysis unit can e.g. be a demodulator, in particular a lock-in amplifier. Here, first detector 10 and second detector 12 can each be coupled with an analysis unit which only filters out signals in the frequency of the modulation signal of the polarization, each with different phase shift, in particular in an embodiment in which beam splitter 13 is a polarization beam splitter.

The apparatus optionally has s second light source 20, the beam path of which is deflected into the beam path of excitation light 5, e.g. by means of a second dichroic mirror 14 that is arranged in the beam path of excitation light 5 and to which the second light source 20 is directed. The second light source 20 can emit a second excitation light, in particular light of a de-excitation wavelength, or light of a switching wavelength, by means of an optical element 21 which may comprise or consist of a second polarization modulator, a phase shift element, and/or a polarization rotation element. With general preference, the second light source 20 is configured to generate light of a de-excitation wavelength so that its polarization is modulated with the modulation signal together with the excitation light 5 by means of the polarization modulator 8, especially with an angle of preferably 90° being configured between the polarization direction of the excitation light 5 and the polarization device of the light of the second light source 20.

The optional optical device 22, as shown schematically, is used e.g. to rotate the polarization of a partial beam of the light produced by the first light source 4 and/or by the second light source 20. With preference, the polarization of light having a de-excitation wavelength, generated by a second light source 20, is rotated. The optical device 22 can be configured for a rotation of the polarization of the partial beam by e.g. >0° to <180°, in particular by 30° to 150°, preferably by 60° to 120°, more preferably by 90°.

FIG. 2 shows the arrangement of a first dichroic mirror 23 and of a second, distanced dichroic mirror 24 in the optical path of excitation light 5 which according to the invention is pointed with a frequency in a polarization plane by the polarization modulator 8. The partial beam 25, deflected by the first dichroic mirror 23, is directed to the second dichroic mirror 24, where in the optical path between the first and the second dichroic mirror 23, 24 at least one optical element 26 is positioned which preferably is a phase shift element that rotates the polarization of the deflected partial beam by 90°, another polarization modulator and/or a polarization rotation element. In particular in this embodiment, the optical paths of excitation and de-excitation light can be guided in a common optical path. In this embodiment, the polarization modulator 8 can consist of 1 polarization modulator 8 in order to generate the identical modulation frequency for excitation and de-excitation light with a fixed phase angle, in particular of 90°, The polarization is shown schematically in FIG. 2 by means of the double arrows.

The first deflection mirror 27 and the second deflection mirror 28 are shown as examples for optical elements that are positioned in the partial beam 25 in order to deflect the partial beam 25 from the first dichroic mirror 23 to the second dichroic mirror 24.

In the examples shown in FIGS. 3 and 4, the excitation light is modulated with a fixed frequency. One period of the signal is an example for a modulation consisting of a signal sequence without any repetition or without periodic repetition. Here, Figures C show the polarization of the excitation light at three points in time $t_1$, $t_2$, $t_3$ and Figures D show the orientation of the dipole moment vectors $r_1$, $r_2$, $r_3$ of three exemplary fluorescent molecules. At parallelism of the polarization of the excitation light to the direction of one of the dipole moment vectors $r_1$, $r_2$, $r_3$, a signal as shown in Figures E and F is produced for the points in time $t_1$, $t_2$, $t_3$. Due to the time shift, the fluorescent molecules, which have been individually excited for emission, are detected individually and are thus spatially separated from each other, leading to an improved resolution of the microscopic representation.

FIG. 3A to F shows the optical analysis for the embodiment of the process in which only excitation light of a first light source 4 is irradiated with frequency modulation on a sample provided with fluorescent molecules and emitted light is detected. FIG. 3A schematically shows the modulated signal as a function of the angle between the linear polarization of the excitation light and the transition dipole moment of a molecule which is also shown linearly in FIG. 3B. FIG. 3C shows the stacked polarization vector of the excitation light which is set up by the modulation at the points in time $t_1$, $t_2$, $t_3$. FIG. 3D shows the stacked dipole moment vectors $r_1$ (parallel to the polarization of the excitation light at 0° at the time $t_1$), $r_2$ (parallel to the polarization of the excitation light at approx. 45° at the time $t_2$), $r_3$ (parallel to the polarization of the excitation light at approx. 135° at the time $t_3$) for one of the three exemplary fluorescent molecules. In FIG. 3D, the fluorescent molecules are coupled to a filament-like sample. The dipole moment vectors for each of the exemplarily shown fluorescent molecules shown in FIG. 3D are parallel to those in FIG. 3C.

FIG. 3E for each of the three fluorescent molecules shows in a box the spatial emission signal that can be detected during the polarization of the irradiated light of a certain orientation. In the first box, the polarization is parallel to $r_1$ while in the boxes below the polarization of the radiated light is oriented in parallel to $r_2$ and $r_3$, respectively. It becomes clear that the modulation of the polarization of the irradiated light leads to an emission only by those fluorescent molecules the dipole moment vector of which is parallel to the polarization. FIG. 3F shows variation over time of the polarization of the light detected for one of the fluorescent molecules each. This presentation of the polarization modulation of the intensity of individual fluorescent molecules makes clear that light is emitted without or with phase shift to the modulation of the polarization of excitation light, and that the demodulation or unfolding, respectively, of the emitted light signal leads to a spatial localization of the fluorescent molecules.

FIGS. 4A to F show the optical analysis for the embodiment of the process in which in addition to the polarization-modulated excitation light, light of light source 20, the polarization of which is shifted by 90° to the polarization of the excitation light, is radiated on a sample provided with fluorescent molecules and emitted light is detected. FIG. 4A to F shows data which correspond to FIG. 3A to F.

Corresponding to FIG. 3A, FIG. 4A shows the modulated signal as function of the angle between the linear polarization of the excitation light and the transition dipole moment of a molecule which is also shown linearly in FIG. 4B. As the light of the second light source has a frequency or a wavelength, respectively, that suppresses or de-excites the emission of fluorescent molecules, this light is also referred to as de-excitation light. In general the irradiation of de-excitation light with a polarization shifted by 90° leads to a limitation of the angle range of the suitably oriented fluorescent molecules. FIG. 4B shows that the modulation becomes sharper due to the polarization-shifted de-excitation light. The representations in FIG. 4D show the dipole moment vectors $r_1$, $r_2$, $r_3$ which correspond to the polarization plane at the points in time $t_1$, $t_2$, $t_3$ of the modulation in FIG. 3C. Furthermore, FIG. 4C also additionally shows the polarization vectors of the de-excitation light, at time $t_1$ the polarization vector at 90°, at time $t_2$ the polarization vector at 135°, and at time $t_3$ the polarization vector at 225°. According to the limitation of the angle range of the suitable oriented fluorescent molecules of FIG. 4A, the angle ranges of the fluorescent molecules are limited or narrower. FIG. 4E shows that the irradiation of the de-excitation light with a polarization shifted to the polarization of the excitation light, or the limitation of the polarization of the excitation light, reduces or prevents the excitation or emission of those fluorescent molecules whose dipole moment vector is not parallel to the polarization of the excitation light while those fluorescent molecules are stimulated for emission whose dipole moment vector lies in parallel to the polarization of the excitation light. FIG. 4E also shows that the demodulated or unfolded detected emission allows for a spatially better resolved presentation without or with phase shift of the polarization, while Figure F shows that the detected emission allows for temporally better resolved representation without or with phase shift of the polarization and therefore a spatially better resolved representation.

FIGS. 3 and 4 also show that the modulation of the polarization of excitation be and the demodulation of detected emission allows for a suppression of unspecific emission and for a spatially resolved detection of individual fluorescent molecules.

The invention claimed is:

1. Apparatus for optical analysis of a sample which contains at least one fluorescent molecule having at least one excitation light source for the generation of excitation light, comprising an optical element which directs the beam path of the excitation light to the sample, a first detector which is arranged in the beam path of the light emitted by the sample, and a polarization modulator that is configured to modulate the polarization of the excitation light with a modulation signal, wherein the first detector is coupled to a signal analysis device that is configured to select the detected signals which are detected with or without phase shift at least at one frequency which is identical to the frequency of the modulation signal or which is set up to select the detected signals which are detected with or without phase shift, which is identical to the modulation signal itself or to a signal derived from the modulation signal.

2. Apparatus according to claim 1, wherein the modulation signal is a periodic sequence of signals having one fixed frequency or having at least two superimposed fixed frequencies, or a sequence of signals that have no repetition.

3. Apparatus according to claim 1, wherein the polarization modulator is a polarizing element rotating with the modulation signal in the beam path of the excitation light, the polarizing element having a linear polarizer, a phase shift element or a combination of at least two mirrors arranged at an angle of 45° to each other, or an acoustic-optical element or an electro-optical element in the optical path of the excitation light and controlled with the modulation signal.

4. Apparatus according claim 1, wherein one of the detectors is arranged in a beam path, which is generated by a first partially transparent mirror arranged in the beam path of irradiation exiting the objective.

5. Apparatus according to claim 1, wherein the light source is configured to generate excitation light of 1 light frequency the multiple of which is the excitation light frequency of the fluorescent molecule, or which is configured to generate excitation light of at least two light frequencies the sum of which is the excitation light frequency of the fluorescent molecule.

6. Apparatus according claim 1, comprising at least one second light source and a first partially transparent mirror arranged in the beam path between the excitation light source and the optical element which first partially transparent mirror is configured to reflect light of the first and second light source into the beam path directed to the optical element.

7. Apparatus according to claim 6, wherein the first light source and the second light source are polarized linearly and shifted by >0° to <180°, in particular by 90°.

8. Apparatus according to claim 6, wherein the second light source is configured to generate light of a de-excitation wavelength and/or light of a switching wavelength that is specific each for at least one fluorescent molecule.

9. Apparatus according to claim 1, comprising a device for deflecting the beam path of the light from at least one of the first light source and the second light source across the sample.

10. Apparatus according to claim 1, wherein a multifocal element is arranged in the beam path of the excitation light.

11. Apparatus according to claim 1, wherein the analysis unit is set up to site-specifically display in a common representation the emission maxima of the detected emission signals, the emission maxima depending on the modulation signal.

12. Apparatus for optical analysis of a sample which contains at least one fluorescent molecule having at least one excitation light source for the generation of excitation light, comprising an optical element which directs the beam path of the excitation light to the sample, a first detector which is arranged in the beam path of the light emitted by the sample, and a polarization modulator that is configured to modulate the polarization of the excitation light with a modulation signal, further comprising a second detector which is arranged in the beam path of the emitted light and which is coupled to a signal analysis device which is configured to select those detected signals that are detected with or without phase shift at least at one frequency which is identical to the frequency of the modulation signal, or which is configured to select the detected signals that are detected with or without phase shift, which are identical to the modulation signal itself or to a signal derived from the modulation signal.

13. Apparatus according to claim 12, wherein between the first detector and the first mirror a second partially transparent mirror is arranged, with a second detector arranged in optical path reflected therefrom.

14. Apparatus according to claim 13, wherein the second partially transparent mirror is a polarization beam splitter and/or that the first partially transparent mirror is a dichroic beam splitter.

15. Apparatus for optical analysis of a sample which contains at least one fluorescent molecule having at least one excitation light source for the generation of excitation light, comprising an optical element which directs the beam path of the excitation light to the sample, a first detector which is arranged in the beam path of the light emitted by the sample, and a polarization modulator that is configured to modulate the polarization of the excitation light with a modulation signal, wherein the signal analysis device is set up to exclusively select those detected signals that are detected with or without phase shift of at least one frequency that is identical to the frequency of the modulation signal, or which is set up to select the detected signals that are detected with or without phase shift, which are identical to the modulation signal itself or to a signal derived from the modulation signal.

16. Apparatus for optical analysis of a sample which contains at least one fluorescent molecule having at least one excitation light source for the generation of excitation light, comprising an optical element which directs the beam path of the excitation light to the sample, a first detector which is arranged in the beam path of the light emitted by the sample, and a polarization modulator that is configured to modulate the polarization of the excitation light with a modulation signal, wherein in the optical path between the excitation light source and the optical element a first partially transparent dividing mirror is arranged that deflects a part of the light generated by at least one of the first light source and the second light source, at least one deflection mirror is arranged in the part of the excitation light deflected by the first dividing mirror, and a second partially transparent dividing mirror is set up to direct the deflected part of the excitation light, which is reflected by the at least one deflection mirror, into the beam path of the excitation light which is directed onto the optical element, wherein a further polarization modulator, a phase shift element, and/or a polarization rotation element is positioned in the beam path between the first partially transparent dividing mirror and the second partially transparent dividing mirror.

17. Apparatus for optical analysis of a sample which contains at least one fluorescent molecule having at least one excitation light source for the generation of excitation light, comprising an optical element which directs the beam path of the excitation light to the sample, a first detector which is arranged in the beam path of the light emitted by the sample, and a polarization modulator that is configured to modulate the polarization of the excitation light with a modulation signal, further comprising second light source which is configured to generate polarized light of a de-excitation wavelength, the polarization of which is shifted by >0° to <180° to the polarization of the excitation light, wherein the polarization modulator is configured to modulate the polarization of the de-excitation light with the modulation signal of the excitation light and wherein the light having de-excitation wavelength is directed into the optical element.

18. Apparatus according to claim 17, configured to irradiate in ring-shape the de-excitation light generated by the second light source onto the sample with a central directional null.

19. Process for optical analysis of a sample, in particular by means of an apparatus according to claim 1, wherein the sample comprises at least one fluorescent molecule, by irradiating excitation light onto the sample and detecting the light emitted by the sample, wherein the modulation of the polarization of the excitation light with a modulation signal, wherein the detection comprises the selection of signals that are detected with or without phase shift at least at one frequency that is identical to the frequency of the modulation signal or which are identical to the modulation signal itself or which are detected at a signal derived from the modulation signal.

20. Process according to claim 19, wherein light, the polarization of which is shifted by >0° to <180° to the polarization of the excitation light, is irradiated onto the sample with modulation of its polarization by the modulation signal.

21. Microscopic representation, obtainable by a process according to claim 19.

22. Apparatus for optical analysis of a sample which contains at least one fluorescent molecule having at least one excitation light source for the generation of excitation light, comprising an optical element which directs the beam path of the excitation light to the sample, a first detector which is arranged in the beam path of the light emitted by the sample, and a polarization modulator that is configured to modulate the polarization of the excitation light with a modulation signal, wherein the first detector is coupled to a signal analysis device that is configured to select the detected signals which are detected with or without phase shift at least at one frequency which is identical to the frequency of the modulation signal or which is set up to select the detected signals which are detected with or without phase shift, which is identical to the modulation signal itself or to a signal derived from the modulation signal, and wherein a second light source which is configured to generate polarized light of a de-excitation wavelength, the polarization of which is shifted by >0° to <180° to the polarization of the excitation light, wherein the polarization modulator is configured to modulate the polarization of the de-excitation light with the modulation signal of the excitation light and wherein the light having de-excitation wavelength is directed into the optical element.

* * * * *